United States Patent [19]

Muetterties et al.

[11] 4,353,369

[45] Oct. 12, 1982

[54] VENIPUNCTURE DEVICE

[75] Inventors: Andrew J. Muetterties, Gages Lake; Joseph N. Genese, Waukegan; Charles H. Seberg, Libertyville, all of Ill.

[73] Assignee: Abbott Laboratories, North Chicago, Ill.

[21] Appl. No.: 112,970

[22] Filed: Jan. 17, 1980

[51] Int. Cl.³ .............................................. A61M 5/00
[52] U.S. Cl. .................. 128/214.4; 128/221; 128/DIG. 26
[58] Field of Search ............. 128/214.4, 214 R, 214.2, 128/214.4, DIG. 26, 221

[56] References Cited

U.S. PATENT DOCUMENTS

| | | | |
|---|---|---|---|
| 2,725,058 | 11/1955 | Rathkey | 128/214.4 |
| 3,064,648 | 11/1962 | Bujan | 128/214.4 |
| 3,313,299 | 4/1967 | Spademan | 128/214.4 |
| 3,537,451 | 11/1970 | Beck | 128/214.4 |
| 3,589,361 | 6/1971 | Loper | 128/214.4 |
| 3,640,275 | 2/1972 | Burke | 128/214 R |
| 3,714,945 | 2/1973 | Stanley | 128/221 |
| 3,774,604 | 11/1973 | Danielsson | 128/214.4 |
| 3,782,383 | 1/1974 | Thompson | 128/221 |
| 4,015,600 | 4/1977 | Llautaud | 128/214 R |
| 4,046,144 | 12/1978 | McFarlane | 128/214 R |
| 4,129,128 | 12/1978 | McFarlane | 128/214 R |
| 4,194,504 | 3/1980 | Harms | 128/214.4 |
| 4,250,880 | 2/1981 | Gordon | 128/214 R |

Primary Examiner—Richard J. Johnson
Attorney, Agent, or Firm—Robert S. Beiser; Robert L. Niblack

[57] ABSTRACT

An improved venipuncture device comprises a catheter having a catheter hub at one end, with a needle having a needle hub at one end and a sharpened tip at the second end extending through the catheter and catheter hub. A resilient reseal is mounted in the catheter hub for sealing the catheter upon removal of the needle. The improvement comprises a wing hub having an axial bore adapted for telescopic reception and attachment to the catheter portion. A pair of oppositely extending flexible wings are integrally formed and extend from the wing hub. An area of reduced thickness on each of the flexible wings along a portion of the width of the wings adjacent to the wing hub allows the wings to be easily folded upward. As a result, the wings may be pinched together between the thumb and index finger, thus, making it easier to insert the needle into the vein of the patient.

6 Claims, 6 Drawing Figures

VENIPUNCTURE DEVICE

BACKGROUND OF THE INVENTION

The present invention relates generally to catheter insertion devices, and more particularly to improvements in catheter insertion devices which facilitate gripping of the device and thereby insertion of a catheter into the vein of the patient.

Heretofore, devices such as wing structures and tapes have been employed to aid in intravenous needle placement and to secure the needle to the skin after venipuncture. Exemplary of the prior art are U.S. Pat. No. 2,725,058—Intravenous Needle Assembly, A. S. Rathkey, issued Nov. 29, 1955; U.S. Pat. No. 3,064,648—Intravenous Needle Assembly, A. F. Bujan, issued Nov. 20, 1962; U.S. Pat. No. 3,589,361—Intravenous Catheter Unit With Flexible Wing Support and Insertion Means, Douglas A. Loper et al., issued June 29, 1971; and U.S. Pat. No. 3,537,451—Intravenous Catheter Unit With Releasable Inserter Means, Dale F. Beck, et al., issued Nov. 3, 1970.

A problem has been found in the past in manufacturing wings that are sufficiently flexible to enable easy gripping and puncture of the patient's vein in use, while at the same time being fixedly attached to a catheter device. Additionally, it has been found that a particular size of wings is not particularly well adapted for taping to certain portions of the anatomy. Accordingly, it is an advantage of the present invention in providing a pair of flexible wings and wing hub in a modular assembly which is easily attachable to catheter devices. It is an additional advantage of the invention to provide such a wing hub and wing hub assembly which is low in cost and easy to manufacture. It is a further advantage of the invention to provide a wing and wing hub assembly in a variety of sizes which are attachable to catheter devices in order to facilitate taping of said devices to various portions of the anatomy.

SUMMARY OF THE INVENTION

The present invention relates generally to venipuncture devices and more particularly to winged catheter devices. The invention comprises a catheter having a catheter hub at its proximal end with a needle having a needle hub at its proximal end extending coaxially through the catheter hub and catheter. A resilient reseal member is attached to the catheter at its proximal end. The present invention represents an improvement over the prior art in the use of a wing hub member having an axial bore therethrough adapted for telescopic reception and attachment to the previously mentioned catheter. A pair of oppositely extending flexible wings are attached to the wing hub. Each wing has an area of reduced thickness along a portion of the width of the wing adjacent to the wing hub. The area of reduced thickness facilitates folding of the wing together, making it easier to hold the catheter from above during venipuncture.

In a preferred embodiment, the catheter hub has a tubular portion extending distally, which is attached to the catheter itself. This tubular portion is approximately equal in diameter to the axial bore of the wing hub member. As a result, the wing hub member may be press-fit onto and thereby fixedly attached to the tubular portion of the catheter hub. An additional feature of the invention is the fact that the wing hub is removable and replaceable in the catheter, so that a variety of wing sizes may be employed with a particular catheter in order to select the proper size for attachment to various portions of the patient's body, i.e., leg, shoulder, chest or wrist.

An additional feature of the invention is a tab member integrally formed and extending from the wing hub member. This tab is constructed and arranged so as to be easily manipulable by the movement of a single finger. As a result, the tab may be used to separate the catheter portion of the device from the needle portion by holding onto the needle hub while moving the tab member away from the needle hub with a single finger.

In a preferred embodiment, the flexible wings and wing hub member are composed of a resilient flexible plastic material such as polyethylene, polypropylene, polybutadiene or polyvinylchloride. As a result, the wing hub member may include a snap locking mechanism for selective attachment of the wing hub to the catheter as desired. The tubing may be also compressed between the wings during venipuncture.

An additional embodiment of the invention encompasses the use of a flexible wing and wing hub assembly for use with an intravenous needle assembly. A hollow needle having a hub attached at its proximal end and a sharpened tip at its distal end is inserted through the axial bore of the wing hub. Again an area of reduced thickness on the wings facilitates the folding thereof.

The invention further includes a method of performing venipuncture utilizing the previously described catheter device. The method comprises the steps of pinching the flexible wing members upward between the thumb and index finger of the user. The needle and catheter then are partially inserted into the vein of the patient. The flexible wing members may then be released. The needle hub is then grasped between the thumb and middle finger of the user and the posterior tab member on the wing hub is pushed forward with the index finger, thereby separating the needle hub from the catheter hub and consequently withdrawing the sharpened tip of the needle within the catheter. The catheter may then be easily inserted further into the vein of the patient.

DETAILED DESCRIPTION OF THE PREFERRED EMBODIMENT

Figure 1:
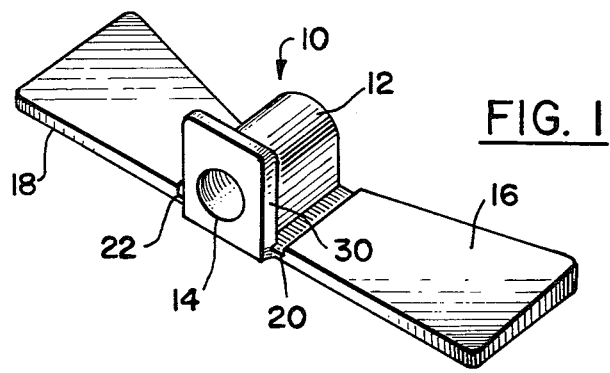
FIG. 1 of the drawings is a front perspective view of a modular wing and wing hub assembly.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

Improved venipuncture device 10, as shown in FIG. 1, comprises a wing hub member 12 having an axial bore 14 extending therethrough adapted for telescopic reception of an attachment to a catheter. A pair of oppositely extending flexible wing sections 16 and 18 are flexibly attached to wing hub member 12. One means of such flexible attachment is the presence of areas of reduced thickness 20 and 22 on flexible wing sections 16 and 18 along a portion of the width thereof adjacent to wing hub member 12. Areas of reduced thickness 20 and 22 allow wings 16 and 18 to be folded upward together and easily held. As a result, a unique method of venipuncture in which the catheter is gripped from above by the flexible wing sections may be utilized, thereby facilitating the performance of such venipuncture. It should be noted in this regard that the present invention represents a distinct improvement over prior art catheter devices having flexible wings. Wings 16 and 18 of the present device 10 are constructed of a flexible resilient material, such as polyethylene or polyvinylchloride, which is ideally suited for bending while at the same time is sufficiently stiff to lay flat for taping purposes against the skin. The use of modular wing hub 12 and wings 16 and 18 allows a different material to be used in the construction of catheter hub 26. As a result, a strong plastic material such as transparent rigid PVC may be utilized for catheter hub 26. An additional feature of the invention is that by having a modular wing hub 12 and wings 16 and 18, a variety of sizes of wings may be chosen in order to properly fit the wings of the site of venipuncture; i.e., legs, chest or wrist.

Figure 2:
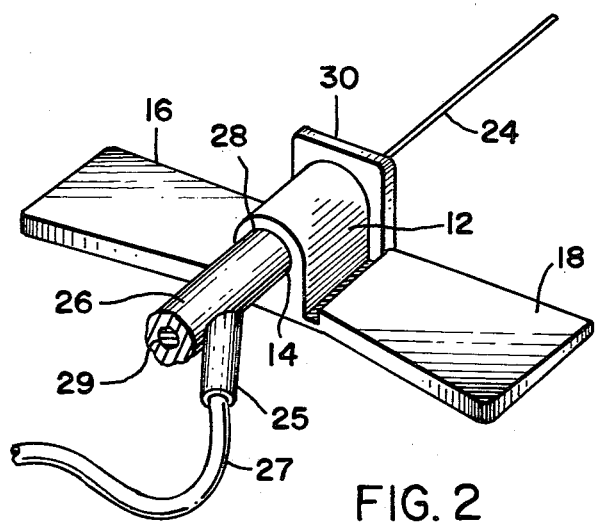
FIG. 2 of the drawings is a rear perspective view of a Y-catheter, telescopically inserted into the modular wing hub assembly of FIG. 1.

As shown in FIG. 2 of the drawings, axial bore 14 of wing hub member 12 is constructed and arranged for telescopic reception of a catheter such as catheter 24. Catheter 24 is attached to a catheter hub 26. Catheter hub 26 has a tubular portion 28 with an outside diameter approximately equal to the inside diameter of axial bore 14. As a result, tubular portion 28 may be press-fit into and thereby fixedly attached to wing hub member 12. In addition, catheter 24 as shown has additive port 25 extending therefrom with flexible tubing 27 attached thereto for use as an alternative channel into the catheter 24. penetrable reseal member 29 is of the type commonly used in intravascular catheters such as that shown in U.S. Pat. No. 3,313,299 to R. G. Spademan which comprises a block of resilient rubber or silicone rubber which reseals the aperture remaining after removal of needle 32. This type of reseal is commonly known in the prior art. Penetrable reseal member 29 is preferably constructed of resilient rubber or silicone rubber so as to reseal the aperture remaining after removal of needle 32.

Figure 3:
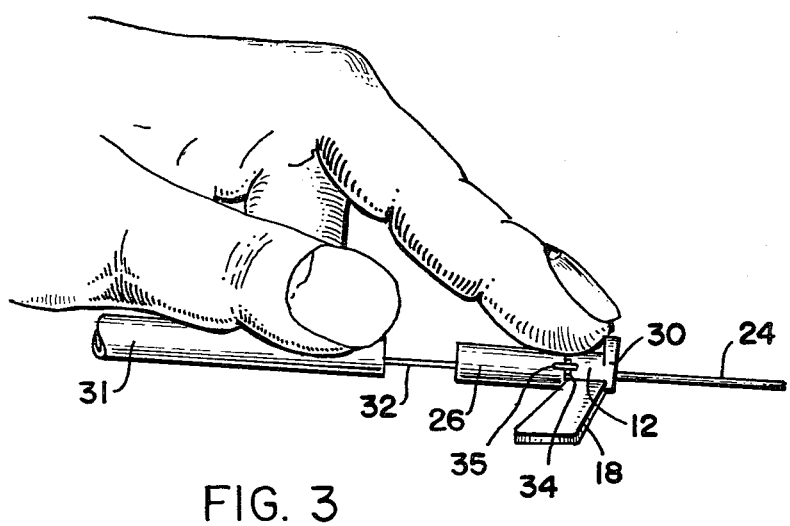
FIG. 3 of the drawings is a side view, partially broken away, of a needle and a needle hub being separated from the catheter and wing hub assembly of FIG. 2.

As best seen in FIG. 3 of the drawings, wing hub 12 includes a tab 30 extending vertically therefrom. Tab 30 is constructed and arranged to be pushed by a single finger in order to separate catheter hub 26 from needle hub 31 and needle 32. As seen in FIG. 3, in operation needle hub 31 is grasped between the thumb and middle finger of the user. The index finger may then be used to push catheter hub 26 forward, so as to withdraw needle 32 out of catheter 24. Alternatively, catheter hub 26 may be held in place by pushing against tab 30 while needle hub 31 and needle 32 are withdrawn from catheter hub 26.

As best seen in FIG. 3 of the drawings, wing hub member 12 may include a plurality of snap locks such as snap lock 34 for selective attachment or detachment of wing hub 12 to catheter hub 26. In the embodiment shown, snap lock 34 comprises a rectangular appendage extending from the proximal portion of wing hub 12, having a tip 35 adapted for slidable engagement with a corresponding aperture in catheter hub 26.

Figure 4:
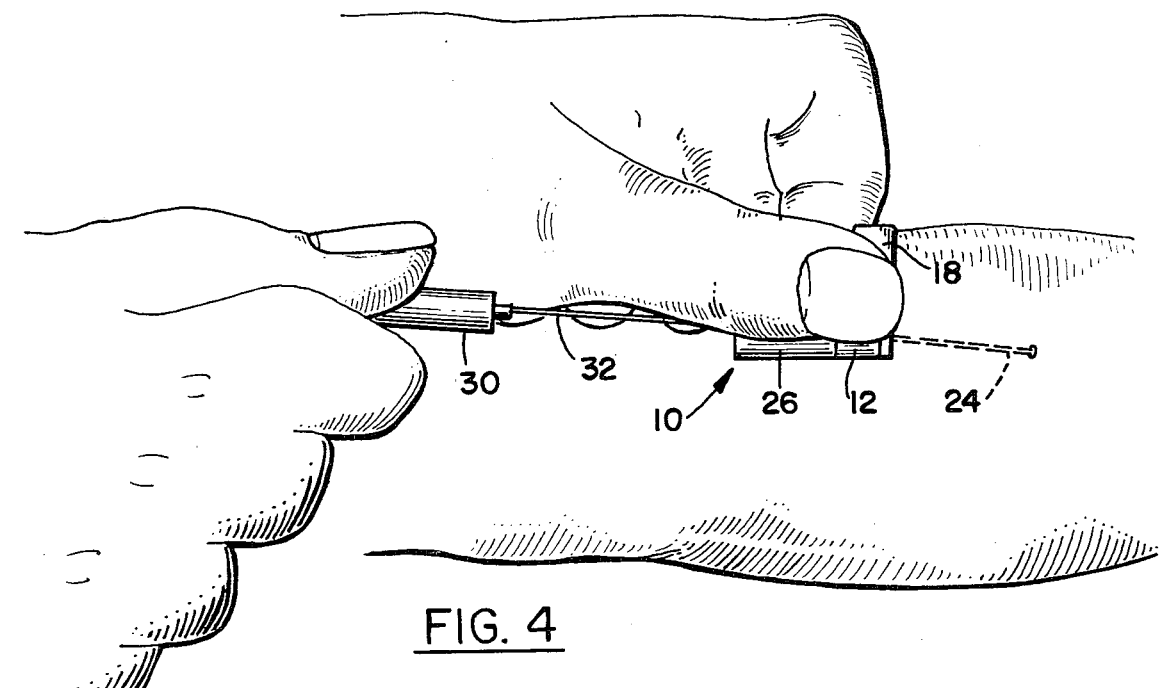
FIG. 4 of the drawings is a side schematic view of a needle and needle hub being separated from the catheter and catheter hub of FIG. 2.

As seen in FIG. 4 of the drawings, improved venipuncture device 10 is also adapted for two-handed separation of catheter hub 26 from needle hub 31. As shown, flexible wings 16 and 18 are raised vertically about wing hub 12 and grasped between the thumb and index finger of user. Needle 32 with catheter 24 coaxially disposed thereabout may then be inserted into the vein of the patient. Once needle 32 and catheter 24 are inserted into the vein, wings 16 and 18 may be held in place while needle hub 31 is drawn away from catheter hub 26. This is accomplished usually with the thumb and the index finger of the second hand of the user. As a result, needle 12 is withdrawn from the device, allowing flexible catheter 24 to be easily inserted further into the vein of the patient.

Figure 5:
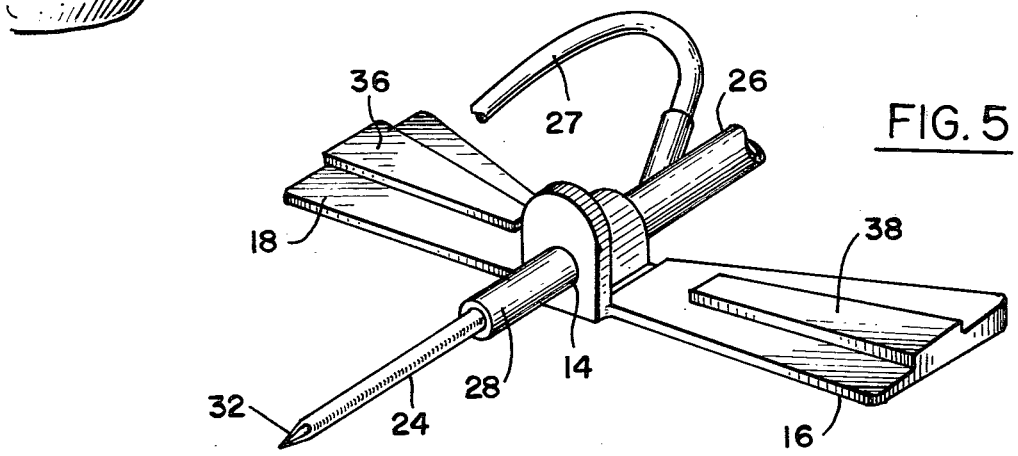
FIG. 5 of the drawings is a front perspective view of an alternative embodiment of the modular wing hub assembly of FIG. 1 showing a portion of the tab extended from the wing hub in a curved configuration.

As best seen in FIG. 5 of the drawings, flexible wings 16 and 18 may include raised sections 36 and 38 which are adapted for compressing a portion of flexible tubing 27 therebetween, so as to prevent the flow of liquid through the tubing. Raised sections 36 and 38 compress flexible tubing 27 when flexible wings 16 and 18 are folded into a vertical position, thereby causing them to be oppositely disposed against the flexible tubing.

Figure 6:
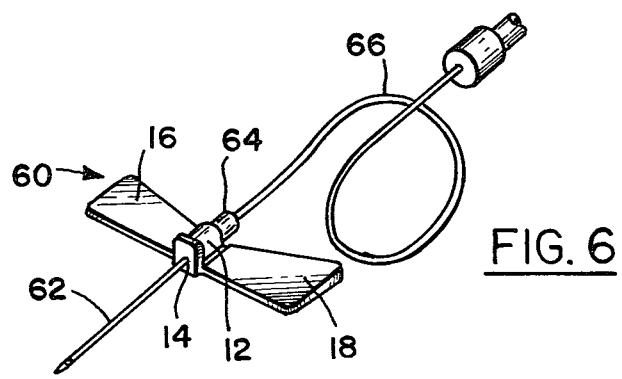
FIG. 6 of the drawings is a front perspective view of a flexible tubing and needle set telescopically received by and attached to the modular wing hub assembly of FIG. 1.

As best seen in FIG. 6 of the drawings, in an alternative embodiment, the invention may also comprise an intravenous needle assembly 60, comprising a hollow needle 62 fixedly attached to and extending from needle hub 64. A length of flexible tubing 66 extends from the proximal portion of needle hub 64. Axial bore 14 extending through wing hub 12 is adapted for telescopic reception of and attachment to needle hub 64. Again, flexible wings 16 and 18 are oppositely disposed from wing hub 12 and are adapted for gripping when raised in a vertical position. A venipuncture technique is thus permitted in which the hollow needle is gripped from above, so as to have more precise control of the angle and force supplied during venipuncture.

The foregoing description and drawings merely explain and illustrate the invention, and the invention is not limited thereto, except insofar as the appended claims are so limited as those skilled in the art, who have the disclosure before them, will be able to make modifications and variations therein without departing from the scope of the invention.

I claim:
1. An improved venipuncture device comprising:
   a needle portion including needle hub means at its proximal end and a sharpened tip at its distal end,
   a catheter portion having a catheter hub means at its proximal end with a reseal member fixedly attached thereto, said needle portion extending coaxially through said catheter portion;
   a modular wing assembly defining a wing hub member having an axial cylindrical bore therethrough adapted for telescopic reception of and attachment to said catheter hub portion;

said catheter hub means having a tubular portion at its distal end adapted for telescopic insertion and attachment to said modular wing assembly, and means for mechanically removably locking said modular wing assembly to said tubular portion whereby said tubular portion may be removably locked onto and thereby fixedly attached to said modular wing assembly; and a pair of oppositely extending flexible wing sections flexibly attached to said wing hub member, said flexible wing sections having an area of reduced thickness on each of said flexible wing sections along a portion of the width thereof, substantially adjacent to said wing hub member, said area of reduced thickness being effective to facilitate the folding of said flexible wing sections together so as to be easily held thereby facilitating insertion of said device into the patient's vein.

2. The venipuncture device according to claim 1 further comprising:

a tab member integrally formed and extending from said modular wing assembly, said tab member being constructed and arranged for digital application of force thereon so as to facilitate separation of said needle portion from said catheter portion.

3. The invention according to claim 1 in which said modular wing assembly comprises a substantially flexible plastic material.

4. The invention according to claim 2 further comprising:

a tab member integrally formed and extending from said modular wing assembly, said tab member being constructed and arranged for the digital application of force thereon so as to facilitate insertion of said device into the patient's vein.

5. An improved venipuncture device comprising:

a needle portion including needle hub means at its proximal end and a sharpened tip at its distal end, a catheter portion having a catheter hub means at its proximal end with a reseal member fixedly attached thereto, said needle portion extending coaxially through said catheter portion;

a modular wing assembly defining a wing hub member having an axial bore therethrough adapted for telescopic reception of and attachment to said catheter hub portion;

said catheter hub means having a tubular portion at its distal end adapted for telescopic insertion and attachment to said modular wing assembly, said tubular portion having an outside diameter approximately equal to the inside diameter of said axial bore of said modular wing assembly whereby said tubular portion may be press-fit into and fixedly attached to said modular wing assembly; and a pair of oppositely extending flexible wing sections flexibly attached to said wing hub member, said flexible wing sections having an area of reduced thickness on each of said flexible wing sections along a portion of the width thereof, substantially adjacent to said wing hub member, said area of reduced thickness being effective to facilitate the folding of said flexible wing sections together so as to be easily held thereby facilitating insertion of said device into the patient's vein.

said wing hub member and said catheter portion having snap lock means for the selective attachment of said wing hub member to said catheter portion.

6. A method of performing venipuncture utilizing an improved venipuncture device comprising a needle portion having hub means at its proximal end and a sharpened tip at its distal end and a catheter portion having said needle portion extending coaxially therethrough, a pair of oppositely extending flexible wing sections fixedly attached to a wing hub member having an axial bore therethrough, said catheter portion being coaxially disposed through and attached to said wing hub member, said wing hub member further having a tab member attached to and extending from said wing hub member, said method comprising the steps of:

pinching said flexible wing members between the thumb and index finger of the user;

inserting said needle portion and said catheter portion partially into the vein of the patient;

releasing said flexible wing members;

grasping said needle hub means between the thumb and middle finger of the user;

pushing said posterior tab member by means of the index finger of the user, thereby separating said needle hub from said catheter portion and consequently withdrawing said sharpened tip within said catheter; and inserting said catheter portion further into the vein of the patient.

* * * * *

UNITED STATES PATENT AND TRADEMARK OFFICE
CERTIFICATE OF CORRECTION

PATENT NO. : 4,353,369
DATED : October 12, 1982
INVENTOR(S) : Andrew J. Muetterties, et al.

It is certified that error appears in the above—identified patent and that said Letters Patent is hereby corrected as shown below:

Column 5, line 33, Claim 4 should read:

a tab member integrally formed and extending normally from

Signed and Sealed this

Twenty-fifth Day of January 1983

[SEAL]

Attest:

Attesting Officer

GERALD J. MOSSINGHOFF
Commissioner of Patents and Trademarks